(12) United States Patent
Rademacher et al.

(10) Patent No.: US 9,220,262 B2
(45) Date of Patent: Dec. 29, 2015

(54) USE OF ACYLCYCLOHEXANEDIONE CARBOXYLIC ACID OR SALTS THEREOF IN COMBINATION WITH ACYLCYCLOHEXANEDIONE CARBOXYLIC ACID ESTERS FOR IMPROVING THE DEVELOPMENT OF GRAMINEOUS PLANTS

(75) Inventors: Wilhelm Rademacher, Limburgerhof (DE); Dieter Strobel, Herxheim am Berg (DE)

(73) Assignee: BASF SE, Ludwigshafen (DE)

( * ) Notice: Subject to any disclaimer, the term of this patent is extended or adjusted under 35 U.S.C. 154(b) by 43 days.

(21) Appl. No.: 13/120,743

(22) PCT Filed: Sep. 25, 2009

(86) PCT No.: PCT/EP2009/062450
§ 371 (c)(1),
(2), (4) Date: Mar. 24, 2011

(87) PCT Pub. No.: WO2010/034813
PCT Pub. Date: Apr. 1, 2010

(65) Prior Publication Data
US 2011/0177947 A1    Jul. 21, 2011

(30) Foreign Application Priority Data
Sep. 26, 2008   (EP) .................................. 08165281

(51) Int. Cl.
*A01N 37/10*   (2006.01)
*A01N 37/42*   (2006.01)

(52) U.S. Cl.
CPC ............. *A01N 37/42* (2013.01); *A01N 37/10* (2013.01)

(58) Field of Classification Search
CPC ..................................................... A01N 37/10
USPC ........................................ 504/142, 144, 189
See application file for complete search history.

(56) References Cited

U.S. PATENT DOCUMENTS

| | | | |
|---|---|---|---|
| 4,560,403 A | 12/1985 | Motojima et al. | |
| 4,584,013 A | 4/1986 | Brunner | |
| 4,618,360 A | 10/1986 | Brunner | |
| 4,623,382 A | 11/1986 | Brunner | |
| 4,678,496 A | 7/1987 | Motojima et al. | |
| 4,693,745 A | 9/1987 | Brunner | |
| 4,803,268 A * | 2/1989 | Brunner et al. | 544/58.4 |
| 4,866,201 A | 9/1989 | Motojima et al. | |
| 6,458,746 B1 * | 10/2002 | Rademacher et al. | 504/128 |
| 2003/0013611 A1 * | 1/2003 | Brinkman | 504/348 |
| 2009/0131519 A1 | 5/2009 | Rademacher et al. | |

FOREIGN PATENT DOCUMENTS

| | | |
|---|---|---|
| AU | 68004 | 12/1989 |
| EP | 0 123 001 | 10/1984 |
| EP | 0 126 713 | 11/1984 |
| EP | 0 338 986 | 10/1989 |
| EP | 0 434 613 | 6/1991 |
| EP | 0 607 094 | 7/1994 |
| WO | WO 2007/009988 | 1/2007 |

OTHER PUBLICATIONS

International Search Report prepared in International Application No. PCT/EP2009/062450, filed Sep. 25, 2009.
International Preliminary Report on Patentability from corresponding International Application No. PCT/EP2009/062450, filed Sep. 25, 2009.

* cited by examiner

*Primary Examiner* — Johann R Richter
*Assistant Examiner* — Danielle Sullivan
(74) *Attorney, Agent, or Firm* — Brinks Gilson & Lione

(57) ABSTRACT

The present invention relates to the use of a combination of acylcyclohexanedionecarboxylic acids or salts thereof and acylcyclohexanedionecarboxylic esters for improving the development of gramineae. The invention also relates to a method for improving the development of gramineae, in which the plants or plant parts thereof are treated with this combination.

2 Claims, No Drawings

USE OF ACYLCYCLOHEXANEDIONE CARBOXYLIC ACID OR SALTS THEREOF IN COMBINATION WITH ACYLCYCLOHEXANEDIONE CARBOXYLIC ACID ESTERS FOR IMPROVING THE DEVELOPMENT OF GRAMINEOUS PLANTS

This application is a National Stage application of International Application No. PCT/EP2009/062450 filed Sep. 25, 2009, the entire contents of which is hereby incorporated herein by reference. This application also claims priority under 35 U.S.C. §119 to European Patent Application No. 08165281.0, filed Sep. 26, 2008, the entire contents of which is hereby incorporated herein by reference.

The present invention relates to the use of a combination of acylcyclohexanedionecarboxylic acids of the formula I described below or salts thereof and acylcyclohexanedionecarboxylic esters of the formula II described below for improving the development of gramineae. The invention also relates to a method for improving the development of gramineae, in which the plants or plant parts thereof are treated with this combination.

The use of acylcyclohexanediones as individual active ingredients, for example prohexadione-calcium or trinexapac-ethyl, for growth regulation in plants is known. For instance, both EP-A-123001 and EP-A-126713 describe the use of acylcyclohexanedione compounds of the general formula

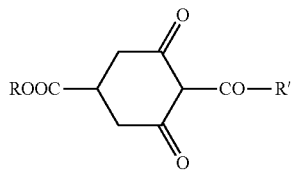

in which
R is hydrogen, alkyl, alkylthioalkyl or optionally substituted phenyl; and
R' is alkyl, optionally substituted benzyl, phenethyl, phenoxymethyl, 2-thienylmethyl, alkoxymethyl or alkylthiomethyl;
or salts thereof as growth regulators.

However, the use of these individual active ingredients is associated with some disadvantages. For instance, prohexadione-calcium does have a rapid onset of shoot-shortening action and leads to enhanced root growth, but the persistence, i.e. the duration of action, is unsatisfactorily short, such that it is necessary to aftertreat repeatedly within one season in order to maintain the desired growth-regulating effect. The persistence of trinexapac-ethyl is longer, but the growth-regulating action sets in with a delay; an additional factor is that, in the harvest of plants which have been treated with trinexapac-ethyl, residues of this active ingredient can be detected, which is of course undesirable.

It was an object of the present invention to provide compounds for the improvement of the development of plants, especially growth-regulating compounds, which combine the abovementioned advantages of the individual active ingredients but avoid their disadvantages. At the same time, it should be possible to reduce the application rate to achieve the same effect.

The object is achieved by the combined use of acylcyclohexanedionecarboxylic acids or salts thereof and acylcyclohexanedionecarboxylic esters.

The invention therefore provides for the use of at least one compound I

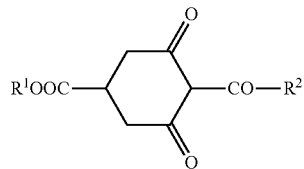

in which
$R^1$ is H; and
$R^2$ is $C_1$-$C_{10}$-alkyl or $C_3$-$C_{10}$-cycloalkyl;
and/or of at least one salt thereof in combination with at least one compound II

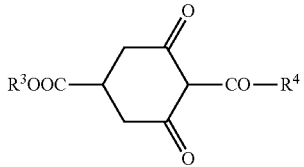

in which
$R^3$ is $C_1$-$C_{10}$-alkyl; and
$R^4$ is $C_1$-$C_{10}$-alkyl or $C_3$-$C_{10}$-cycloalkyl;
for improving the development of gramineae.

The combined use of acylcyclohexanedionecarboxylic acids of the formula I and/or salts thereof and acylcyclohexanedionecarboxylic esters of the formula II may firstly consist in using a composition which comprises these two active ingredients.

The invention therefore also provides for the use of a composition comprising at least one acylcyclohexanedionecarboxylic acid of the formula I and/or at least one salt thereof and at least one acylcyclohexanedionecarboxylic ester of the formula II for improving the development of gramineae.

On the other hand, the combined use of acylcyclohexanedionecarboxylic acids of the formula I and/or salts thereof and acylcyclohexanedionecarboxylic esters of the formula II may also consist in employing the two active ingredients separately, but in close correlation in terms of space and time. Further details of the combined use of acylcyclohexanedionecarboxylic acids of the formula I or salts thereof and acylcyclohexanedionecarboxylic esters of the formula II can be found in the remarks which follow.

The invention further provides a method for improving the development of gramineae, which comprises applying at least one compound of the formula I and/or at least one salt thereof and at least one compound of the formula II in a mixture or separately, simultaneously or successively in the form of an aqueous spray liquor to the plants or plant parts thereof.

In the context of the present invention, $C_1$-$C_{10}$-alkyl represents a linear or branched alkyl radical having 1 to 10 carbon atoms, such as methyl, ethyl, propyl, isopropyl, n-butyl, sec-butyl, isobutyl, tert-butyl, pentyl, neopentyl, hexyl, heptyl, octyl, 2-ethyl-hexyl, nonyl or decyl. $C_1$-$C_4$-Alkyl represents methyl, ethyl, propyl, isopropyl, n-butyl, sec-butyl, isobutyl or tert-butyl. The alkyl radical is preferably linear.

$C_3$-$C_{10}$-Cycloalkyl represents a cycloaliphatic radical having 3 to 10 carbon atoms as ring members. Examples are cyclopropyl, cyclobutyl, cyclopentyl, cyclohexyl, cycloheptyl, cyclooctyl, cyclodecyl and decalin. $C_3$-$C_6$-Cycloalkyl represents a cycloaliphatic radical having 3 to 6 carbon atoms as ring members. Examples are cyclopropyl, cyclobutyl, cyclopentyl and cyclohexyl.

Acylcyclohexanedione compounds of the formulae I and II are known from EP-A 0 123 001 and from EP-A 126 713.

The compounds of the formulae I and II may be present both in the trione form (triketo form) a and in the tautomeric keto-enol forms b and c:

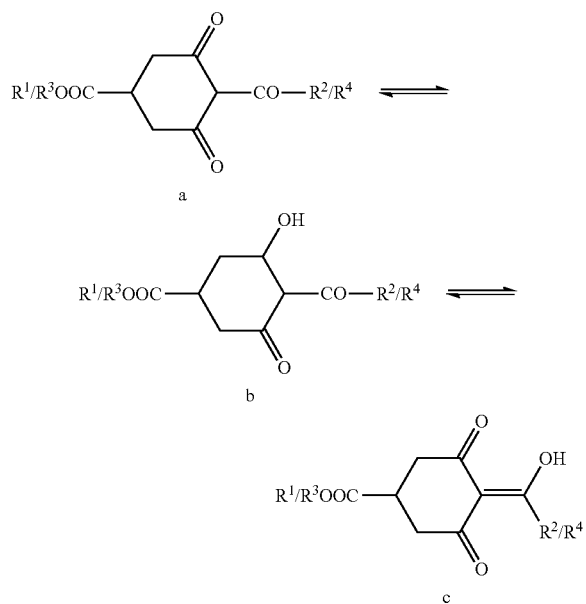

The salts of the acylcyclohexanedione compounds I may be the salts either of the monoanions or of the dianions of these compounds. The monoanions may be present either as carboxylate anions I.d or as enolate anions I.e or I.f:

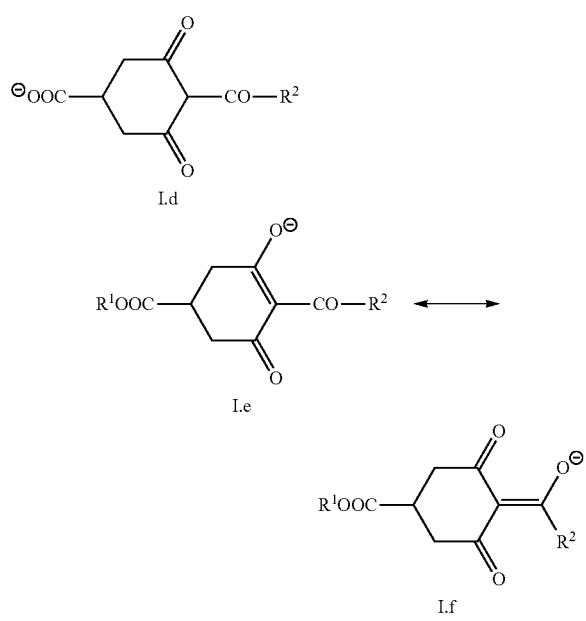

In the dianion, the carboxylate and the enolate groups are accordingly present alongside one another.

Preferred cations in the salts of the compounds of the formula I are the ions of the alkali metals, preferably of lithium, sodium and potassium, of the alkaline earth metals, preferably of calcium and magnesium, and of the transition metals, preferably of manganese, copper, zinc and iron, and also ammonium ($NH_4+$) and substituted ammonium, in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethyl-ammonium, diisopropylammonium, trimethylammonium, tetramethylammonium, tetraethylammonium, tetrabutylammonium, 2-hydroxyethylammonium, 2-(2-hydroxyeth-1-oxy)eth-1-ylammonium, di(2-hydroxyeth-1-yl) ammonium, benzyltrimethylammonium, benzyltriethylammonium, and additionally phosphonium ions, sulfonium ions, preferably tri($C_1$-$C_4$-alkyl)sulfonium such as trimethylsulfonium, and sulfoxonium ions, preferably tri($C_1$-$C_4$-alkyl)sulfoxonium. Preferred cations are also chlormequat [(2-chloroethyl)trimethylammonium], mepiquat (N,N-dimethylpiperidinium) and N,N-dimethyl-morpholinium. Particularly preferred cations are the alkali metal cations, the alkaline earth metal cations and the ammonium cation ($NH_4+$). The compound is especially the calcium salt.

In the context of the present invention, the term "compounds of the formula I" and "acylcyclohexanedione of the formula I" refers both to the uncharged compounds I and to the salts thereof.

In the compounds of the formula I, $R^1$ is preferably H or in a formal sense represents one calcium equivalent (i.e. ½ $Ca^{2+}$).

$R^2$ is preferably $C_1$-$C_4$-alkyl or $C_3$-$C_6$-cycloalkyl and especially ethyl or cyclopropyl. Compounds I for use with particular preference in accordance with the invention are prohexadione ($R^1$=H, $R^2$=ethyl), prohexadione-calcium (calcium salt of prohexadione), trinexapac ($R^1$=H, $R^2$=cyclopropyl) and trinexapac-calcium (calcium salt of trinexapac). Especially prohexadione-calcium is used. However, the latter is converted essentially to prohexadione on contact with water.

In the compounds II, $R^3$ is preferably $C_1$-$C_4$-alkyl and especially ethyl.

$R^4$ is preferably $C_1$-$C_4$-alkyl or $C_3$-$C_6$-cycloalkyl, and especially ethyl or cyclopropyl.

Compounds II for use with particular preference in accordance with the invention are prohexadione-ethyl ($R^3$=ethyl, $R^4$=ethyl) and trinexapac-ethyl ($R^3$=ethyl, $R^4$=cyclopropyl). Especially trinexapac-ethyl is used.

The improvement in the development of the plants treated in accordance with the invention can be demonstrated by one or more criteria. An improved development is understood to mean the achievement of a state of the plant which leads to an economic, health or esthetic advantage over the state of the same plant which, however, has not been treated in accordance with the invention but grows under otherwise the same conditions. It should be noted that the improvement of the state or of the development of the plant is not attributable to a herbicidal, fungicidal or insecticidal effect of the acylcyclohexanedione combination used in accordance with the invention.

In one embodiment of the invention, the improved development of the plants treated in accordance with the invention is attributable to the growth-regulating action of the combined use of acylcyclohexanediones of the formulae I and II.

The invention thus preferably provides for the use of at least one acylcyclohexanedione of the formula I and/or of at least one salt thereof in combination with at least one acyl-cyclohexanedione of the formula II for growth regulation in gramineae.

According to the plant type, the growth-regulating action may be manifested in different effects. These include
the limitation of shoot growth;
the promotion of root growth;
a yield increase through redistribution of assimilates from the shoots into the growing fruits.

The term "fruit" relates to all plant products, which serve primarily for plant propagation and are of economic significance to humans, such as fruits in the narrower sense, grains, seeds and nuts.

"Shoots" refer generally to parts of a plant which usually grow above ground, project or protrude vertically upward or else are adjacent to the ground, and later develop leaves and lignify in the case of woody species such as trees. In the context of the present invention, the term "shoot" refers, with regard to reduced growth, usually to reduced growth of the shoot axis. The shoot axis is the rod-shaped part in which, in the multitude of cases, the stela for water conduction or for sugar transport are present, and which consists of a plurality of sections, the internodes, which are delimited from one another by thickened sites, the nodes. They are known as stems in herbaceous plants, as trunks, branches and twigs in woody species, and as scion or sprout at the juvenile stage.

In the case of plants cultivated in fall or winter (such as winter rape or winter cereals, such as winter wheat), the limitation of shoot growth reduces copious growth and in this way minimizes cold and frost damage (i.e. by the reduction of the attack area). In the case of cereals, a shortened shoot reduces lodging of the plants (the stems bending over). This improves the harvestability and reduces the infection risk through soil bacteria. Since lodging generally also leads to a deterioration in the grain quality (poorer ratio of starch to protein content; lower 1000 grain weight), a shortened shoot also leads to an improvement in the grain quality. In the cultivation of sugarcane, the shortening of the shoot leads to an earlier harvest, as a result of which the plants become more homogeneous and can thus be harvested with a lower level of machinery and personnel demands. In the case of lawn grasses, longer cutting intervals are possible.

The promotion of root growth increases the stability of the plants; this is of significance especially for cereals; lawn grasses form a more durable turf. The promotion of root growth may consist either in the formation of a longer main root or in greater branching of the root (more highly developed root system). The promotion of root growth can be assessed, for example, by the determination of the dry biomass of the root. Higher root growth also enables more intensive absorption of water and nutrient salts from additionally covered soil regions as a result of the increased absorption area.

In the case of virtually all plants, redistribution of assimilates from the shoot into the fruits/grains takes place, which leads to an enhanced yield. Moreover, redistribution of assimilates from the shoot into the root generally also takes place, which promotes root growth, which again leads to the abovementioned positive effects.

The growth-regulating effects mentioned may of course be interdependent. For instance, the shortening of the shoots can promote assimilate enrichment in the fruit and/or the root. However, not all connections are known for all plant types, and so the individual aspects are considered separately here.

In a preferred embodiment, the invention relates to the use of the at least one compound of the formula I or the salt thereof in combination with the at least one compound of the formula II for growth regulation in gramineae, especially for limiting shoot growth and/or for promoting root growth. The invention more preferably relates to the use of the at least one compound of the formula I or the salt thereof in combination with the at least one compound of the formula II for preventing lodging in the case of cereals. The invention more preferably relates to the use of the at least one compound of the formula I or the salt thereof in combination with the at least one compound of the formula II additionally to increase the yield and/or to improve the grain quality in the case of cereals. The invention more preferably relates to the use of the at least one compound of the formula I or the salt thereof in combination with the at least one compound of the formula II also for maturity control in sugarcane cultivation. In the context of the present invention, "improving the grain quality" means, inter alia, increasing the 1000 grain weight and/or improving the ratio of protein to starch content.

According to the invention, gramineae are treated. Gramineae, which are also referred to as poaceae, are grasses and include cereals, sugarcane and field/lawn grasses. Cereals are cultivated grasses and include especially wheat, triticale, rye, barley, oats, rice, corn and millet (*sorghum* and *panicum* species).

The plants are more preferably selected from cereals, even more preferably from wheat, triticale, rye, barley, oats and rice, and especially from wheat, barley, rye, triticale and oats. The cereal is especially wheat.

The plants are preferably treated in such a way that the plant or plant parts thereof are contacted with at least one acylcyclohexanedione compound I or a salt thereof and at least one acylcyclohexanedione compound II. The compounds of the formulae I and II can be applied to the plant or to the plant parts in a mixture or separately. In the case of separate application, the individual active substances can be applied simultaneously or successively, though, in the latter case, the individual components should be applied within a minimum period of time, preferably within a period of time of a few seconds or a few minutes, for example 1, 2 or 3 minutes, up to a few days, for example 1, 2, 3, 4, 5, 6 or 7 days. Preference is given, however, to combined application using a ready-to-use formulation which comprises both components.

The compounds of the formulae I and II are preferably used in combination in a seasonal total application rate of 5 to 1000 g/ha, more preferably of 50 to 500 g/ha and especially of 50 to 250 g/ha. In the case of rice, the particularly preferred application rate is 5 to 50 g/ha.

According to the field of application, it may be advisable to combine the compounds of the formulae I and II with one another in different weight ratios. The weight ratio of all compounds I to all compounds II is preferably 10:1 to 1:10, more preferably 9:1 to 1:9 and especially 7:3 to 3:7. Specifically, the weight ratio of all compounds I to all compounds II is 1.5:1 to 1:1.5 and even more specifically about 1:1.

The active substances are preferably applied 1 to 8 times per season. The number of applications depends on factors including the plant type and species; for instance, in the case of cereals, application is effected more preferably 1 to 4 times and especially 1 to 2 times, and in the case of lawn grasses, in contrast, more preferably 3 to 6 times.

The application dates, the number of applications and the specific application rates used depend on the particular plant type and species and on further parameters, such as weather conditions, availability of water and nutrients, and have to be determined by the person skilled in the art in the individual case.

In the case of cereals, the treatment is effected preferably when the plant is at BBCH growth stage 25 to 49. When a plurality of applications are undertaken, for example two applications, the first application is preferably effected when the plant is at BBCH growth stage 25 to 32, and the second when the plant is at BBCH growth stage 37 to 49 (BBCH stages according to extended BBCH scale; German Federal Institute for Agriculture and Forestry; see www.bba.de/veroeff/bbch/bbch.htm).

The compounds I, II or the mixture thereof are typically used as formulations, as are customary in the crop protection sector. For example, they can be diluted with water in the form of concentrated solutions, suspensions or emulsions, and be applied by spraying. The application forms are guided by the plant type or the plant part to which application is to be effected; in each case, they should ensure, as far as possible, the finest distribution of the compounds used in accordance with the invention.

In addition to the compounds of the formulae I and II, the formulations may comprise formulation auxiliaries customary for the formulation of crop protection compositions, for example inert auxiliaries and/or surface-active substances, such as emulsifiers, dispersants, wetting agents and the like.

Useful surface-active substances include the alkali metal, alkaline earth metal, ammonium salts of aromatic sulfonic acids, e.g. lignosulfonic acid, phenolsulfonic acid, naphthalenesulfonic acid and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols and of fatty alcohol glycol ethers, condensation products of sulfonated naphthalene and derivatives thereof with formaldehyde, condensation products of naphthalene or of the naphthalenesulfonic acids with phenol and formaldehyde, polyoxyethylene octylphenol ether, ethoxylated isooctyl-, octyl- or nonylphenol, alkylphenyl polyglycol ether, tributylphenyl polyglycol ether, alkylaryl polyether alcohols, isotridecyl alcohol, fatty alcohol ethylene oxide condensates, ethoxylated castor oil, polyoxyethylene or polyoxypropylene alkyl ethers, lauryl alcohol polyglycol ether acetate, sorbitol esters, lignosulfite waste liquors or methylcellulose.

Useful inert auxiliaries include essentially:
mineral oil fractions of moderate to high boiling point such as kerosene and diesel oil, and also coal tar oils and oils of vegetable or animal origin, aliphatic, cyclic and aromatic hydrocarbons, e.g. paraffins, tetrahydronaphthalene, alkylated naphthalenes and derivatives thereof, alkylated benzenes and derivatives thereof, alcohols such as methanol, ethanol, propanol, butanol and cyclohexanol, ketones such as cyclo-hexanone, strongly polar solvents, for example amines such as N-methylpyrrolidone, and water.

Aqueous application forms of the inventive preparations can be prepared from storable formulations such as emulsion concentrates, suspensions, pastes, wettable powders or water-dispersible granules, by adding water. To prepare emulsions, pastes or oil dispersions, the active ingredients present in the inventive preparations, as such or dissolved in an oil or solvent, can be homogenized by means of wetting agents, adhesives, dispersants or emulsifiers in water. It will be appreciated that the application forms comprise the auxiliaries used in the storable formulations.

To promote the absorption of compounds of the formula I into treated plants, acidification of the spray liquor is advantageous. Accordingly, ready-to-use formulations may also comprise suitable acids (e.g. citric acid). Such acids may, however, also be added separately to the spray liquor.

In a preferred embodiment, the compounds I and II used in accordance with the invention are used in the form of an aqueous spray liquor.

The active ingredient combinations used in accordance with the invention are usable for an application in the case of all of the aforementioned gramineae and further plants. Depending on the plant part to which they are applied, they can be applied with equipment which is known per se and customary in agricultural practice, preference being given to application in the form of an aqueous spray solution or spray liquor. An application is effected either to all of the plant part above ground or else only to individual plant parts, such as leaves, blossom or fruits. The selection of the individual plant parts to which application is to be effected depends on the kind of plant and its stage of development, and on the desired effect. Preference is given to treating young vegetative shoot parts.

The invention further provides a composition comprising at least one compound of the formula I and/or at least one salt thereof and at least one compound of the formula II, where the total weight ratio of the at least one compound I or the salt thereof to the at least one compound II is 10:1 to 1:10. With regard to preferred compounds I and II and the salts of the compounds I and preferred weight ratios, reference is made to the above remarks.

The inventive composition may be a physical mixture of the at least one compound I and/or of a salt thereof with at least one compound II. Accordingly, the invention also provides a mixture which comprises the at least one compound I and/or at least one salt thereof and at least one compound II, wherein the total weight ratio of the at least one compound I or the salt thereof to the at least one compound II is 10:1 to 1:10. However, the composition may also constitute any desired combination of the at least one compound I or the salt thereof with at least one compound II, in which I and II are not present formulated together.

One example of an inventive composition in which the at least one compound I or the salt thereof and the at least one compound II are not present formulated together is a two-component kit. Accordingly, the present invention also relates to a two-component kit comprising a first component which comprises the at least one compound I and/or at least one salt thereof, a liquid or solid carrier and optionally at least one interface-active substance and/or at least one customary auxiliary, and a second component which comprises the at least one compound II, a liquid or solid carrier and optionally at least one interface-active substance and/or at least one customary auxiliary. Suitable solid and liquid carriers, interface-active substances and customary auxiliaries are described above.

The compounds I and II can also be used in combination with other growth regulators. For example, in the case of barley and rye, combinations with ethephon have been found to be favorable. Combined application with fungicides, herbicides, insecticides and foliar fertilizers is likewise possible, and saves time for the user.

Through the inventive use of acylhexanediones of the formula I or salts thereof in combination with those of the formula II, it is firstly possible to eradicate the disadvantages of the individual active ingredients; thus, the growth-regulating action sets in very rapidly and continues for a long time; it is also no longer possible to detect any residues of trinexapac (ethyl). Secondly, the positive effects even add up to an effect greater than their sum; i.e. there is a synergistic effect, especially in relation to the growth-regulating action. "Synergistic effect" means that the improvement in the development of the plant in relation to at least one effect is increased to an extent greater than that resulting from addition; in other words, the effect in question occurs to a significantly greater degree than would have been expected proceeding from the expected action of the individual active ingredients I and II. For instance, the growth-regulating effect, especially the shoot shortening and/or the promotion of root growth (enlargement of the root or of the root system) is significantly greater than would have been expected from the growth-regulating effects of the individual active ingredients I and II. Expected efficacies of active ingredient combinations can be determined, for example, by the Colby formula (S. R. Colby, Calculating Synergistic and Antagonistic Response of Herbicide Combinations, Weeds, 15, p. 20-22). The synergistic effect of the active ingredient combination used in accordance with the invention allows the total application rate of the substances to achieve the same effect to be reduced. This in turn leads to even lower active ingredient residues in the harvest of the plants treated.

The examples which follow are intended to illustrate the invention, but without restricting it.

EXAMPLES

Example 1

Reduction of Shoot Growth in Winter Wheat by Combined Use of Prohexadione-Ca and Trinexapac-Ethyl (Greenhouse Test)

Wheat plants of the "Cubus" cultivar were cultivated in pots of diameter 12 cm on a customary growing substrate. The plants were treated at BBCH development stage 11/12 (1-2 leaves unfolded) at a shoot length of 16 cm as a foliar application with a liquid volume of 750 I/ha. Both prohexadione-Ca ("ProCa") and trinexapac-ethyl ("TriEt") were used as technical grade active ingredients. To prepare an applicable spray liquor, the adjuvant LI-700 (Loveland Products, Inc., Greeley, Colo., USA) was added in a concentration of 0.1%. The shoot length of the plants was measured at different times after the treatment. The following results were obtained (data in centimeters):

TABLE 1A

Shoot lengths

| Treatment | Days after treatment - shoot length [cm] | | | |
|---|---|---|---|---|
| [g/ha] | 0 | 5 | 8 | 11 |
| — (control) | 16 | 24.6 | 28.1 | 32.3 |
| ProCa [25] | 16 | 23.0 | 26.6 | 31.1 |
| ProCa [50] | 16 | 23.0 | 26.3 | 29.5 |
| ProCa [100] | 16 | 22.5 | 24.0 | 25.8 |
| TriEt [25] | 16 | 24.6 | 27.9 | 32.9 |
| TriEt [50] | 16 | 24.4 | 26.5 | 31.8 |
| TriEt [100] | 16 | 22.3 | 23.6 | 28.5 |
| ProCa + TriEt [25 + 25] | 16 | 22.8 | 24.5 | 31.4 |
| ProCa + TriEt [50 + 50] | 16 | 22.1 | 24.1 | 28.1 |

TABLE 1B

Efficacy of the composition used in accordance with the invention

| Active ingredient combination [g/ha] | Calculated efficacy[1,2] [%] | Observed efficacy[1] [%] |
|---|---|---|
| ProCa + TriEt [25 + 25] | | |
| 5 days after treatment | 18.6 | 20.9 |
| 8 days after treatment | 13.9 | 29.8 |
| 11 days after treatment | 0 | 5.5 |
| ProCa + TriEt [50 + 50] | | |
| 5 days after treatment | 20.5 | 29.1 |
| 8 days after treatment | 26.1 | 33.1 |
| 11 days after treatment | 19.8 | 25.8 |

[1]% shortening of growth compared to particular control
[2]according to Colby

As the results show, the combined use of the active ingredients leads to a synergistic effect according to S. R. Colby [Weeds 25 (1966): 20-22] on the reduction of shoot growth.

Example 2

Reduction of Shoot Growth and Improved Action Against Lodging in Winter Wheat by Combinations of Prohexadione-Ca and Trinexapac-Ethyl (Field Test)

Winter wheat of the "Bussard" cultivar was cultivated under field conditions. To "provoke" significant lodging, the supply of the nutrient element nitrogen was deliberately selected too high. The remaining growing conditions corresponded to customary practice. The plants were treated with the inventive active ingredient combination at the BBCH 31/32 development stage (1- to 2-node stage) as a foliar application with a liquid volume of 200 I/ha. Prohexadione-Ca ("ProCa") (50 g/ha) was used as Regalis (BASF) and trinexapac-ethyl ("TriEt") (75 g/ha) as Moddus (Syngenta). The shoot length of the plants was measured at various times from the treatment until they were ready for harvest. The following results were obtained (data in centimeters):

TABLE 2A

Shoot lengths

| Treatment [g/ha] | Days after treatment - shoot length [cm] | | | | | | |
|---|---|---|---|---|---|---|---|
| | 0 | 7 | 21 | 30 | 37 | 49 | 63 |
| — (control) | 43.0 | 55.0 | 82.0 | 104.5 | 111.5 | 127.8 | 129.0 |
| ProCa [50] | 43.0 | 50.0 | 69.3 | 89.0 | 99.5 | 119.8 | 120.0 |
| TriEt [75] | 43.0 | 54.5 | 76.3 | 97.8 | 102.8 | 119.8 | 121.0 |
| ProCa + TriEt [50 + 75] | 43.0 | 48.0 | 63.9 | 77.3 | 85.8 | 108.3 | 109.0 |

TABLE 2B

Efficacy of the composition used in accordance with the invention

| Active ingredient combination [g/ha] ProCa + TriEt [50 + 75] | Calculated efficacy[1,2] [%] | Observed efficacy[1] [%] |
|---|---|---|
| 7 days after treatment | 44.1 | 58.3 |
| 21 days after treatment | 42.4 | 46.4 |
| 30 days after treatment | 33.4 | 44.2 |
| 37 days after treatment | 28.0 | 37.5 |
| 49 days after treatment | 17.9 | 23.0 |
| 63 days after treatment | 18.8 | 23.3 |

[1]% shortening of growth compared to particular control
[2]according to Colby

As the results show, the combined use of the active ingredients leads to a synergistic effect over the entire growth of the plants according to S. R. Colby [Weeds 25 (1966): 20-22] on the reduction of shoot growth. The growth-regulating action sets in immediately and persists for so long that no further treatment is required.

For crops ready for harvest from the test, the degree of stem lodging was determined. This value is the product of the percentage area in which the wheat plants are no longer upright with the intensity of lodging (0=plants are upright/ 100=plants lie flat on the ground) divided by 100. The values obtained here likewise lead to the conclusion of a synergistic interaction of the active ingredients involved:

| Treatment [g/ha] | Degree of lodging | Improvement over control | |
|---|---|---|---|
| | | absolute | [%] |
| Control | 91 | 0 | 0 |
| ProCa [50] | 81 | 10 | 11 |
| TriEt [75] | 93 | ./. | ./. |
| ProCa + TriEt [50 + 75] | 73 | 18 | 20 |

The invention claimed is:

1. A composition comprising prohexadione-calcium and trinexapac-ethyl in a weight ratio of 1:1 to 1:1.5.

2. A method for reducing shoot growth of gramineae, which comprises applying a composition of claim 1.

* * * * *